(12) United States Patent
Fourt et al.

(10) Patent No.: US 10,179,209 B2
(45) Date of Patent: Jan. 15, 2019

(54) INJECTION NEEDLE COVERING SYSTEM

(71) Applicant: Eli Lilly and Company, Indianapolis, IN (US)

(72) Inventors: Jesse Arnold Fourt, Menlo Park, CA (US); Jeremy Christopher Koehler, Menlo Park, CA (US)

(73) Assignee: Eli Lilly and Company, Indianapolis, IN (US)

( * ) Notice: Subject to any disclaimer, the term of this patent is extended or adjusted under 35 U.S.C. 154(b) by 153 days.

(21) Appl. No.: 15/116,885

(22) PCT Filed: Feb. 6, 2015

(86) PCT No.: PCT/US2015/014722
§ 371 (c)(1),
(2) Date: Aug. 5, 2016

(87) PCT Pub. No.: WO2015/123095
PCT Pub. Date: Aug. 20, 2015

(65) Prior Publication Data
US 2016/0346483 A1 Dec. 1, 2016

Related U.S. Application Data

(60) Provisional application No. 61/938,402, filed on Feb. 11, 2014.

(51) Int. Cl.
*A61M 5/32* (2006.01)
*A61M 5/28* (2006.01)
*A61M 5/50* (2006.01)

(52) U.S. Cl.
CPC .......... *A61M 5/3202* (2013.01); *A61M 5/288* (2013.01); *A61M 5/326* (2013.01); *A61M 5/5086* (2013.01); *A61M 2005/3267* (2013.01)

(58) Field of Classification Search
CPC .. A61M 5/3202; A61M 5/3243; A61M 5/321; A61M 5/326; A61M 2005/3267
See application file for complete search history.

(56) References Cited

U.S. PATENT DOCUMENTS

| 3,134,380 A | 5/1964 | Armao |
| 4,775,369 A | 10/1988 | Schwartz |

(Continued)

FOREIGN PATENT DOCUMENTS

| DE | 19856167 | 5/2000 |
| JP | 2006180904 | 7/2006 |

(Continued)

OTHER PUBLICATIONS

Patent Cooperation Treaty International Search Report and Written Opinion of the International Searching Authority, pertaining to International Application No. PCT/US2015/014722; dated Apr. 16, 2015.

*Primary Examiner* — Laura A Bouchelle
(74) *Attorney, Agent, or Firm* — Daniel Spillman

(57) ABSTRACT

A needle covering system for a needle of a syringe. A boot of the system defines a contaminant-proof pocket for the needle. A sealing ring portion of the boot forms a seal with a support portion of the syringe. A body of the boot is collapsible to allow movement of a needle pierceable end portion of the boot toward the sealing ring portion for a tip of the needle to pass through the boot end portion for an injection. A securement collar of the system presses the sealing ring against the support portion of the syringe and is a remnant portion of a protective shell.

20 Claims, 11 Drawing Sheets

(56) References Cited

U.S. PATENT DOCUMENTS

| | | | | |
|---|---|---|---|---|
| 4,915,697 A | * | 4/1990 | DuPont | A61M 5/326 |
| | | | | 604/192 |
| 5,135,496 A | * | 8/1992 | Vetter | A61M 5/34 |
| | | | | 604/111 |
| 5,549,568 A | | 8/1996 | Shields | |
| 5,554,134 A | * | 9/1996 | Bonnichsen | A61M 5/24 |
| | | | | 604/232 |
| 5,616,135 A | | 4/1997 | Thorne et al. | |
| 5,807,347 A | | 9/1998 | Bonaldo | |
| 6,398,762 B1 | * | 6/2002 | Vetter | A61M 5/002 |
| | | | | 604/171 |

FOREIGN PATENT DOCUMENTS

| | | |
|---|---|---|
| WO | 199317739 | 9/1993 |
| WO | 199611026 | 4/1996 |
| WO | 2013028936 | 2/2013 |
| WO | 2013032779 | 3/2013 |
| WO | 2014159018 | 10/2014 |

* cited by examiner

INJECTION NEEDLE COVERING SYSTEM

BACKGROUND OF THE INVENTION

The present invention pertains to pharmaceutical injection devices, and, in particular, to a system for covering a needle of an injection device.

Patients suffering from a number of different diseases frequently must inject themselves with pharmaceuticals. A variety of devices are available to facilitate these injections, such as simple prefilled needled syringes used alone, or automatic injection devices that when triggered by a user automatically insert into the user a needle of a prefilled syringe that prior to triggering was disposed within the automatic injection device housing, and then automatically inject a dose of medication through that inserted needle.

To maintain the sterility of the needle of a syringe prior to its use, a variety of needle covers have been proposed. One type of needle cover needs to be removed by a user prior to syringe use. Such a needle cover often has a multipart construction including an inner cover and an outer cover. The inner cover is relatively flexible or elastomeric and provides a sterile barrier around the needle and forms a seal with, for example, the syringe hub from which the needle extends. The inner cover also may seal the tip of the needle such as in designs where the needle is already in fluid communication with the syringe contents. The outer cover is made of a relatively rigid material and protectively surrounds and engages the inner cover. A pulling of the outer cover from the syringe pulls off the inner cover to expose the needle for use. Another example of this type of needle cover is provided as a flexible cover without a rigid cover thereover. While such needle covers are useful, it needs to be removed from the syringe by the user prior to injection which makes it undesirable in some situations.

Another type of needle cover advantageously does not need to be removed by the user from the syringe prior to use. One example of this type of needle cover is known from WO 2013/032779. This type of needle cover is formed of a resilient material and includes a body that is collapsible. When the cover body collapses when pressed against an injection site either directly or indirectly with an apertured portion of the device in which it is used interposed, the tip of the needle within the cover pierces the cover for insertion into the user.

While a needle cover that does not have to be removed by a user is very convenient for a user of the device in which it is disposed, such design is not without potential shortcomings. For one thing, a collapsible needle cover for a needled syringe may complicate manufacture. Not only must a flexible needle cover be assembled over the needle, but when so assembled the needle still needs to be protected from damage, and people protected from accidental needle sticks, as the needle cover is handled throughout any remaining processes of manufacture. Still further, unless the needle cover is securely attached around the needle there is a possibility that after such attachment, be it during further manufacture, distribution or use preparation, the needle cover could come off from or lose its needle sterility-maintaining seal with the rest of the device.

Thus, it would be desirable to provide a needle covering system that can overcome one or more of these and other shortcomings of the prior art.

BRIEF SUMMARY OF THE INVENTION

In one form thereof, the present invention provides a needle covering system for a needle of a syringe including a boot and a securement collar. The boot defines a contaminant-proof pocket for the needle. The boot includes a sealing ring portion, a needle pierceable end portion at a base of the pocket, and a body extending between the sealing ring portion and the needle pierceable end portion and having an interior hollow for the needle. The sealing ring portion is structured to form a continuous seal with a support portion of the syringe. The body is collapsible to allow movement of the needle pierceable end portion toward the sealing ring portion for a tip of the needle to pass through the needle pierceable end portion. The securement collar presses the sealing ring portion against the support portion of the syringe. The securement collar is a remnant portion of a protective shell. The remnant portion remains after a disconnection of the remnant portion and a remainder portion of the protective shell during manufacture and the remainder portion is removed from a protective position around the boot body.

One advantage of the present invention is that a needle covering system may be provided which allows for a secure attachment around the needle with which it is used.

Another advantage of the present invention is that a needle covering system may be provided which facilitates handling of a needled device to which it is mounted.

Another advantage of the present invention is that a needle covering system may be provided which is radially compact.

Yet another advantage of the present invention is that a needle covering system may be provided which does not require a number of interconnected separate parts.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein.

Figure 1:
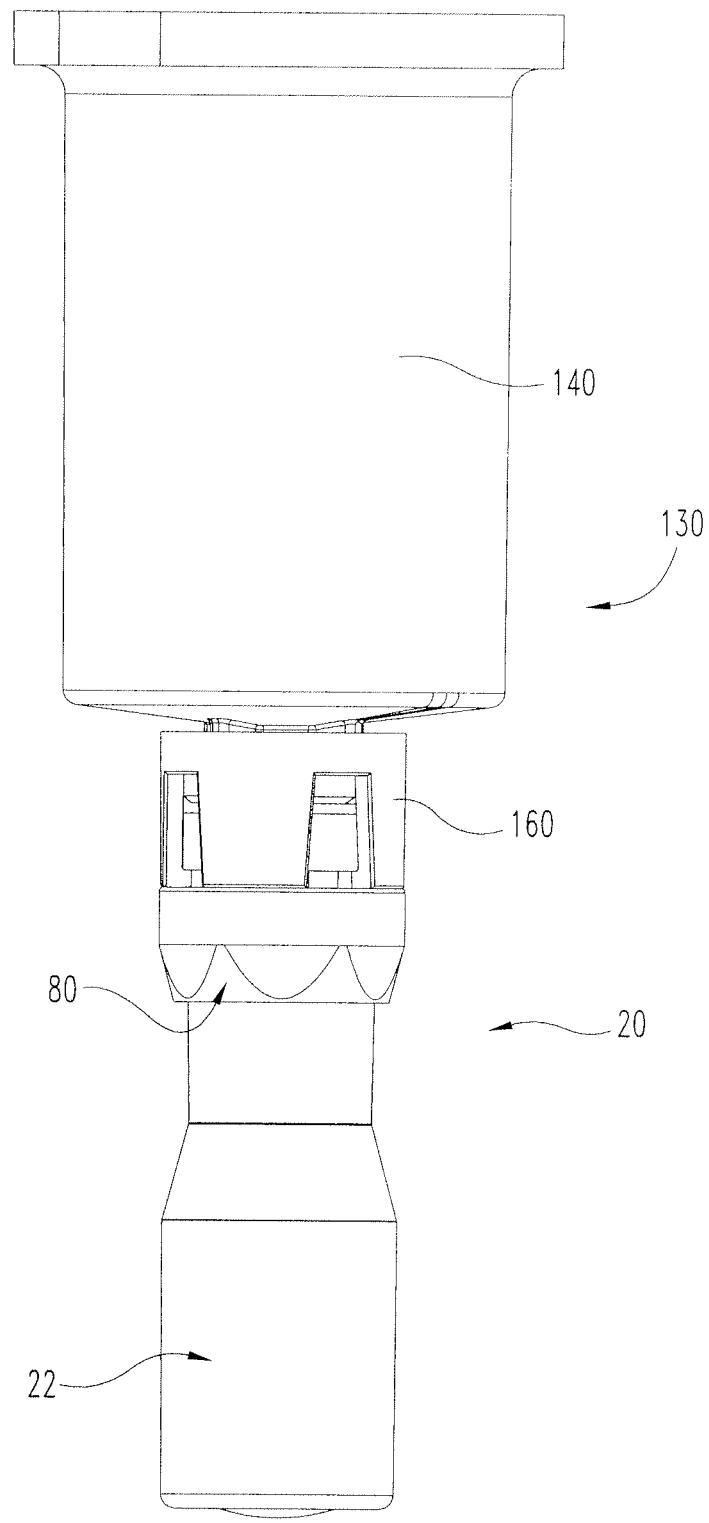
FIG. 1 is a front view of a needled syringe equipped with an injection needle covering system of the present invention prior to use of the syringe to inject its contents.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DETAILED DESCRIPTION OF THE INVENTION

Figure 2:
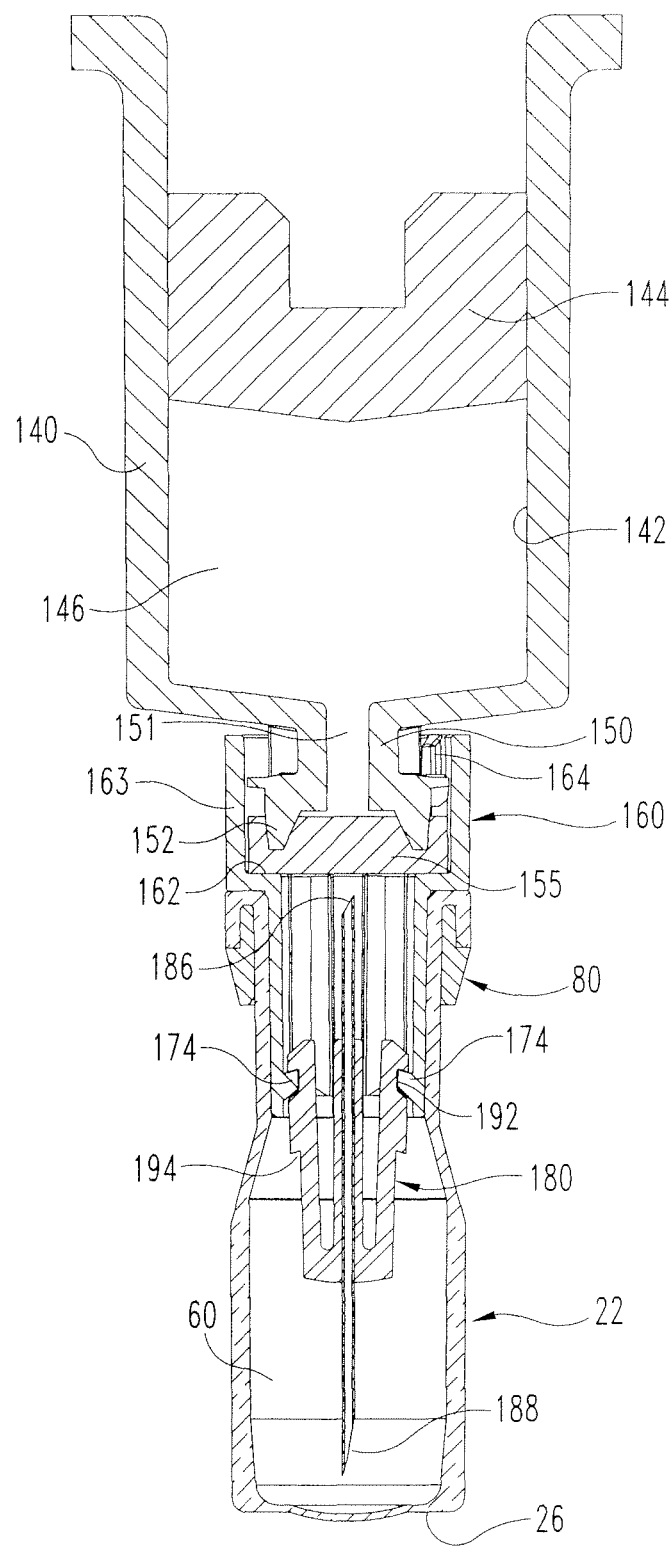
FIG. 2 is a longitudinal cross-sectional view of the needled syringe and injection needle covering system of FIG. 1.
Figure 3:
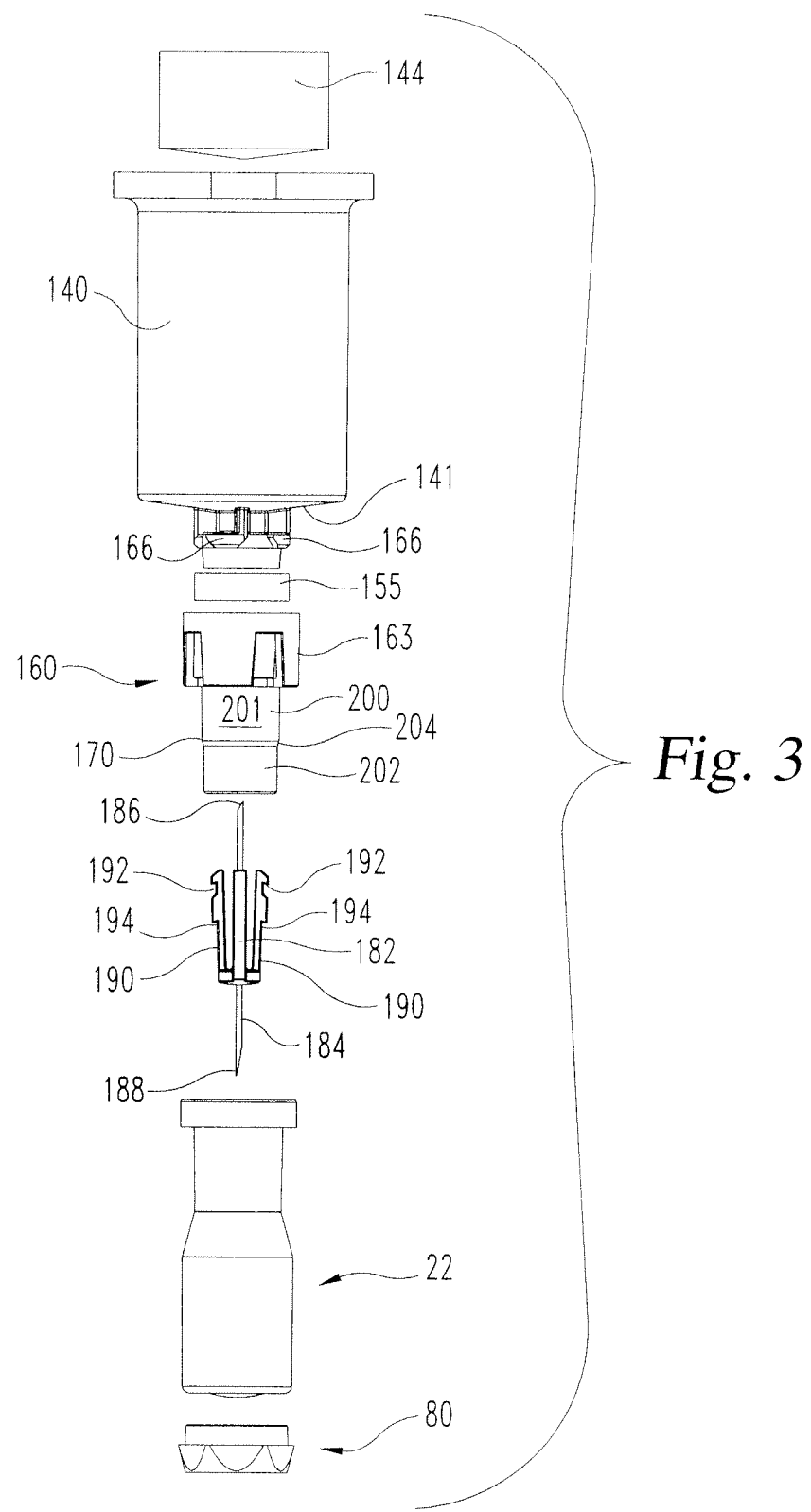
FIG. 3 is a front view similar to FIG. 1 but with the needled syringe and injection needle covering system shown in an exploded arrangement.
Figure 4:
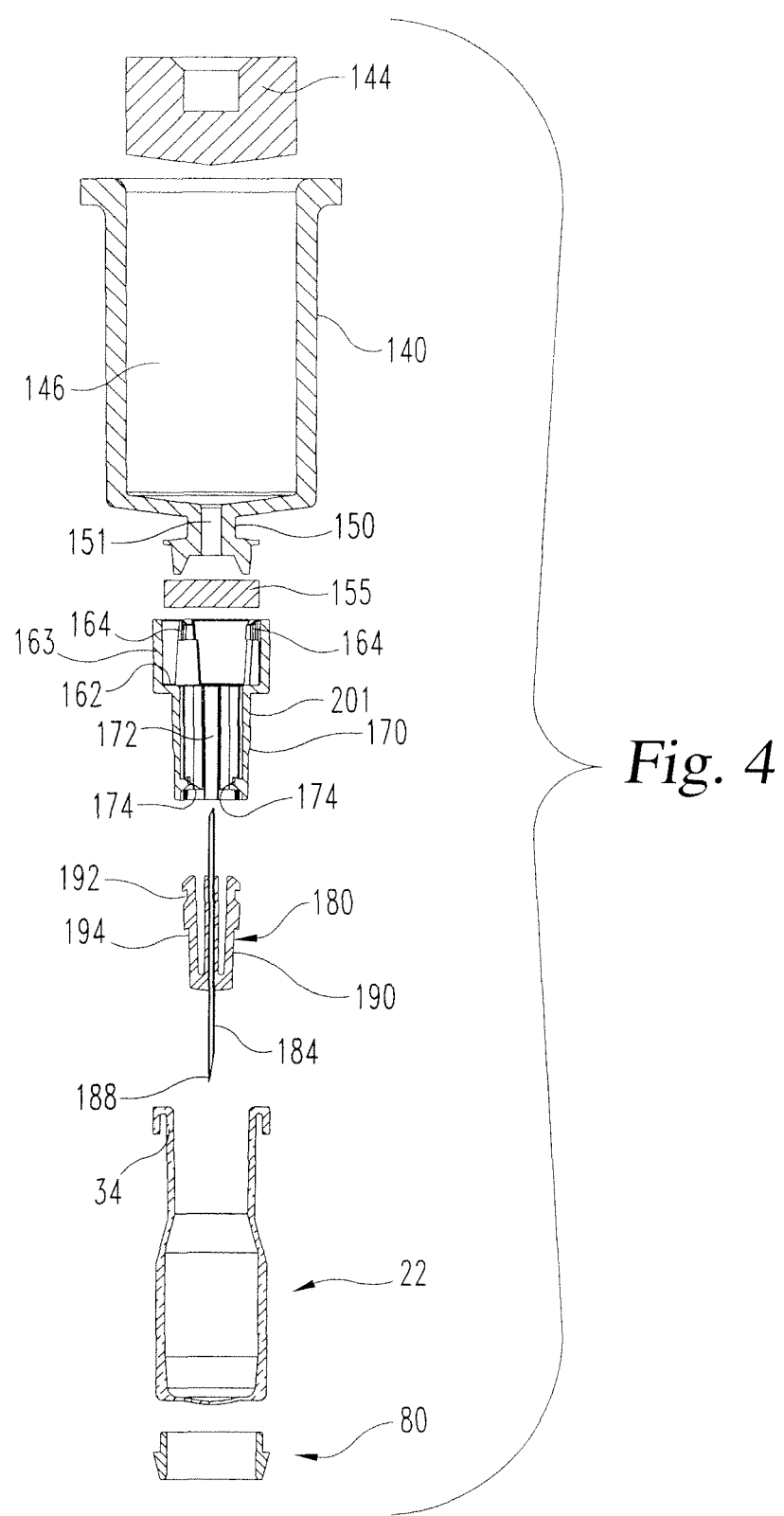
FIG. 4 is a longitudinal cross-sectional view of the needled syringe and injection needle covering system of FIG. 3.

In FIGS. 1 and 2, a first embodiment of an injection needle covering system of the present invention, generally designated 20, is shown installed or mounted to a needled syringe, generally designated 130. Injection needle covering system 20 includes a resilient boot 22 and a securement collar 80, and is intended to maintain the sterility of the needle of needled syringe 130 prior to syringe use. The assembly of needled syringe 130 and covering system 20 of FIGS. 1 and 2 is well suited for use in an automatic injection device as described further below. However, the covering system 20 could be used with different devices, such as standard prefilled syringes, within the scope of the invention.

Figure 5A:
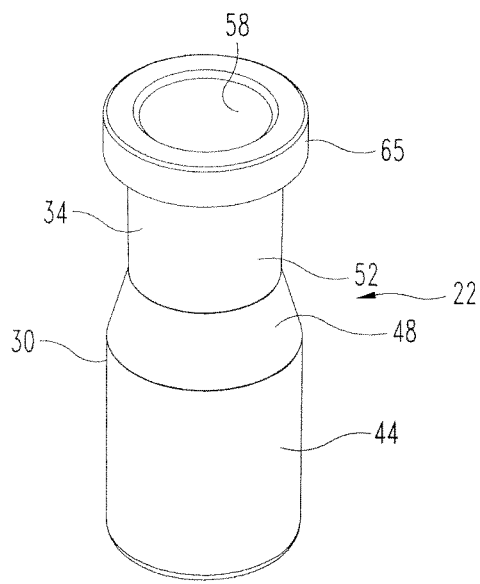
FIGS. 5a, 5b, 5c, 5d and 5e are respectively perspective, front, longitudinal cross-sectional, bottom and top views of a boot of the injection needle covering system of FIG. 1.
Figure 5B:
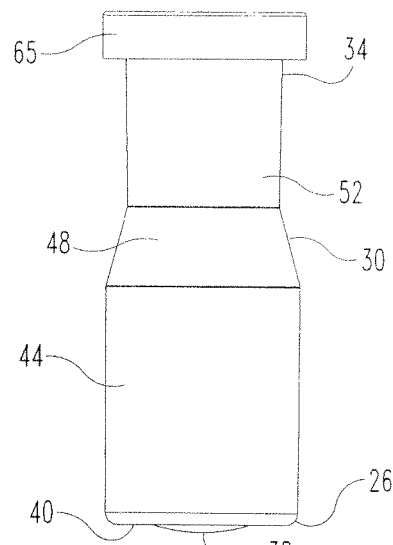
Figure 5C:
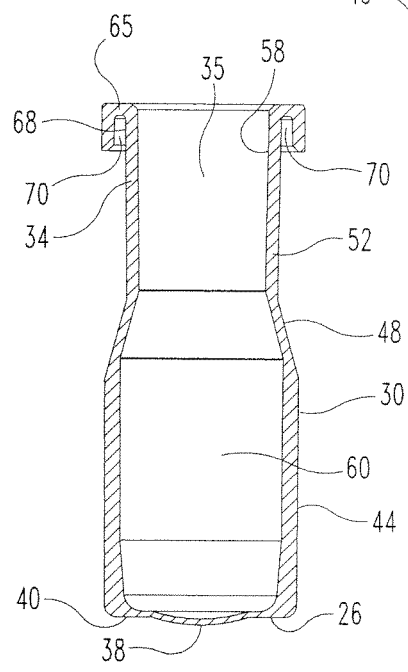
Figure 5D:
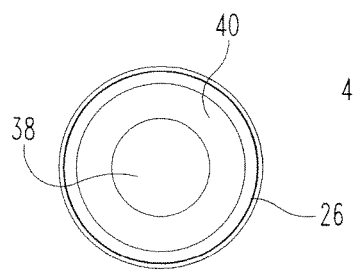
Figure 5E:
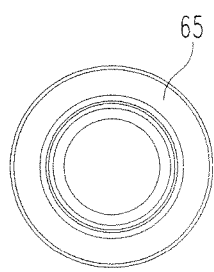
Figure 6A:
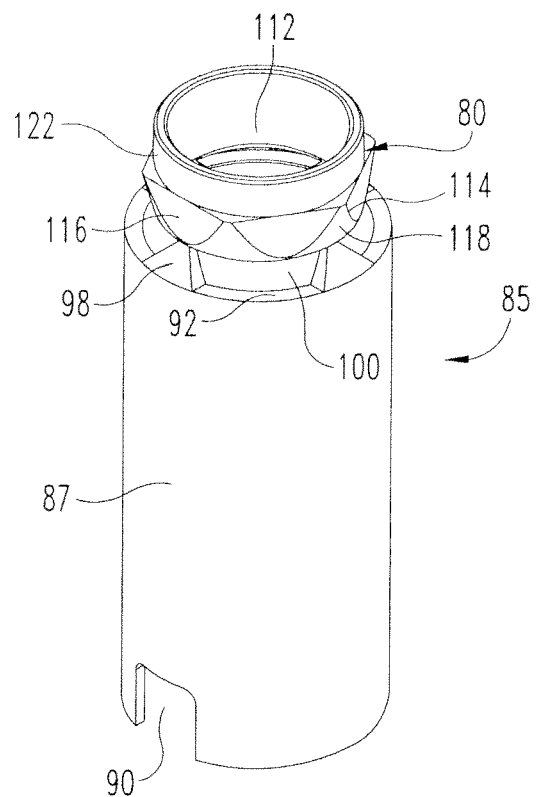
FIGS. 6a, 6b, 6c, 6d and 6e are respectively perspective, front, top, longitudinal cross-sectional taken along line 6d-6d, and longitudinal cross-sectional taken along line 6e-6e views of a protective cover of the injection needle covering system of FIG. 1.
Figure 6B:
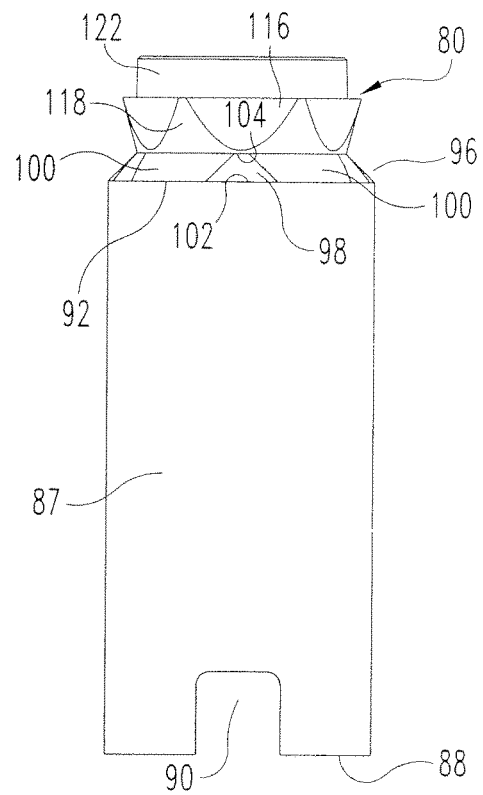
Figure 6C:
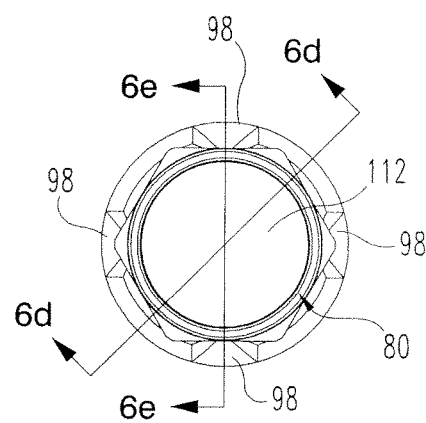
Figure 6D:
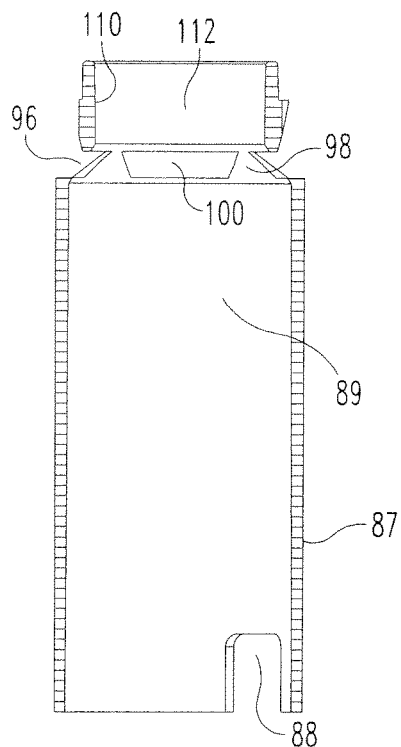
Figure 6E:
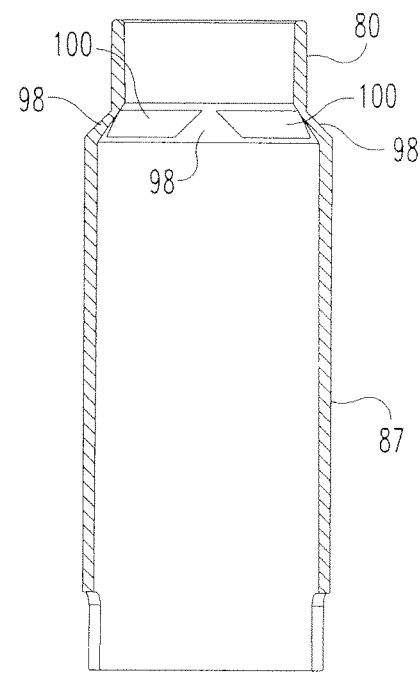

Referring now to FIGS. 5a-5e, boot 22 is made as a single resilient piece out of a compression or injection molded elastomer, such as a liquid injection molded silicone with durometer between 40 and 60 on the shore A scale. Boot 22 is uniformly configured around the longitudinal axis and thus the cross-sectional view shown in FIG. 5c is representative of boot 22 along any longitudinally extending cut plane. Boot 22 includes a disc-shaped distal end 26, a hollow body 30 extending proximally therefrom, and a sealing or mounting region 34 at the proximal end of body 30. The material of boot 22 has no holes such that boot 22 can provide a liquid-tight internal volume when sealing with a syringe support surface. The material of boot 22 may be permeable to sterilizing gases used to sterilize the device needle during manufacture.

Boot distal end 26 has a central region 38 that is thinner than the thickness of the annular region 40 of the distal end surrounding it. The distal tip 188 of syringe needle 184 is intended to pierce or pass through central region 38 during syringe use. Central region 38 is convex distally so as to insertably fill an aperture of a housing end plate of the automatic injection device in which covering system 20 is used, which device aperture also allows passage of the syringe needle tip 188 therethrough during an injection.

Boot body 30 is adapted to collapse in the axial direction during use so as to allow boot distal end 26 to be moved toward boot mounting region 34. Boot body 30 includes a generally cylindrical sleeve-shaped base portion or region 44 that begins at the outer radial periphery of distal end 26 and extends upward in an axial direction therefrom. The inner diameter of the boot body 30 tapers at the distal end. An upper edge of base portion 44 transitions to a boot hinge region 48 that has a frustoconical outer periphery and which in turn transitions to a generally cylindrical sleeve-shaped boot upper portion or region 52. Upper region 52 is formed with a slight taper in inner and outer diameters as it extends distally. The outer radial periphery of upper portion 52 is smaller in circumference than the inner radial periphery of base portion 44 to allow for insertion therein. Hinge region 48 is thinner in construction than either base portion 44 or upper portion 52 to promote it being axially collapsible by folding over itself to allow base portion 44 to pass over hinge region 48 as base portion 44 is shifted proximally relative to needle tip 188. In alternate embodiments, the collapsing aspect of the boot body may be accomplished with other body configurations. For example, a bellows shaped body in which the body compresses in an accordion style may be employed.

An upper edge of body upper portion 52 transitions seamlessly to a boot mounting region 34 that seals with the needled syringe. Boot mounting region 34 is formed with a slight taper in inner and outer diameters as it extends distally. Boot mounting region 34 is ring-shaped and forms a continuous or three hundred and sixty degree seal with a rigid support portion or surface 201 of the needled syringe 130. Mounting region 34 is similar in structure to body upper portion 52 but it differs therefrom in that the body upper portion 52 is located axially below and does not form a seal with the needled syringe support surface 201 described further below.

In the shown embodiment in which the mounting region 34 fits around the outer periphery of a portion of the syringe which serves as the support surface 201, the interior surface 58 of mounting region 34, continuously along its inner circumference, forms the seal with the support surface. Although in the shown embodiment the support surface 201 has a cylindrical outer periphery, differently shaped support surface outer peripheries, such as polygonal ones, can be continuously sealed by their engagement with the entire inner circumference of the mounting region interior surface, which mounting region shape can also be modified if necessary in alternate embodiments to seal therewith.

In still another alternate embodiment, and with modification to the securement collar, the mounting region of the boot may be configured to have an outer radial surface that continuously along its outer circumference sealingly engages a radially inwardly facing needled syringe support surface, with the securement collar being mountable to such support surface by sandwiching the boot mounting region therebetween.

As best shown in FIG. 5c, the interior hollow 35 of mounting region 34 and the interior hollow of boot body 30 result in boot 22 forming a pocket 60 for the syringe needle. Boot distal end 26 forms the closed base of pocket 60, and mounting region 34 forms the mouth of pocket 60. When mounting region 34 seals with the needled syringe the pocket is contaminant-proof so that the needle 184 within the pocket 60 is guarded from contamination by the external environment.

At the proximal end of mounting region 34, boot 22 includes a radially outwardly protruding lip 65 that facilitates handling of the boot. Lip 65 is generally L-shaped and encircles mounting region 34. Lip 65, together with the outer radial periphery 68 of boot mounting region 34, form an annular hollow 70 sized and shaped to accommodate the upper edge of securement collar 80.

Securement collar 80 is a remnant portion of a protective cover or shell generally designated 85 and further shown in FIGS. 6a-6e. Protective cover 85 is a rigid part formed as a single piece, such as an injection molded polystyrene plastic. Cover 85 includes a tubular base 87, a neck region 96 and collar 80. Base 87 is a cylindrical sleeve having an internal hollow 89 sized to freely receive therein the boot body 30.

Figure 8:
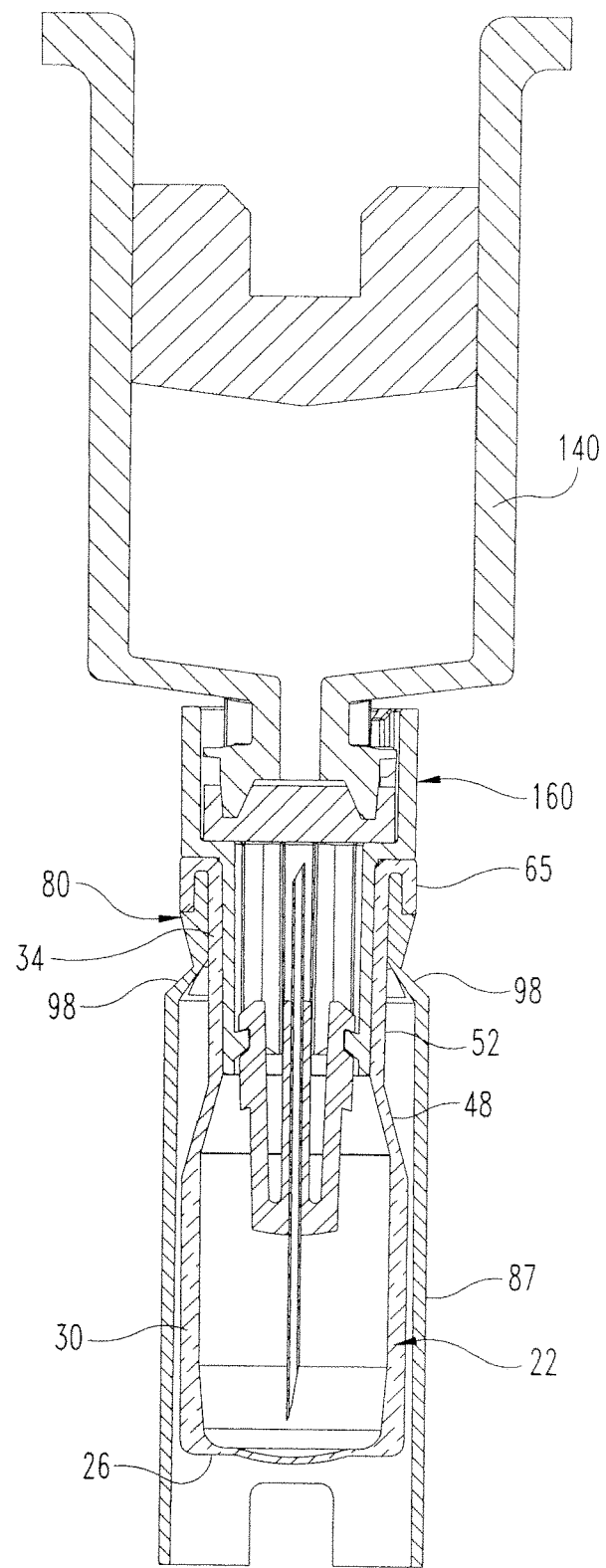
FIG. 8 is a longitudinal cross-sectional view of the needled syringe and injection needle covering system of FIG. 7.

The length of base 87, as shown in FIG. 8, is long enough to protectively house distal needle tip 188 as well as the entire height of boot body 30. A distal end 88 of base 87 has two diametrically arranged notches 90 that end at a proximal location below the boot distal end 26 when the boot is disposed therein. Notches 90 accommodate a tool that allows twisting of cover 85 during use as described below. In an alternate embodiment, notches 90 can be replaced with openings spaced from the distal end 88, which openings allow insertion of a tool that can twist as well as pull base 87 distally.

The tapered neck region 96 of cover 85 extends between the proximal end 92 of base 87 and collar 80. Neck region 96 provides a frangible connection of collar 80 and cover base 87.

In the shown embodiment, the frangible neck region 96 is formed by four triangular flanges 98 that span the distance between collar 80 and base 87. The flanges 98 are spaced at ninety degree intervals around the cover circumference. Openings 100 through the neck region 96 extend between flanges 98 and are larger in circumferential length than flanges 98 to form a major portion of the neck region circumference. Each triangular flange 98 has a large leg region 102 formed with base proximal end 92, and a tip portion 104 formed with collar 80. The shorter circumferential length of tip portion 104 as compared to the circumferential length of leg region 102, which is in a ratio of about ⅕ in the shown embodiment, results in tip portion 104 cleanly breaking or shearing from collar 80, instead of leg region 102 breaking from base 87, when collar 80 and base 87 are sufficiently and intentionally twisted relative to each other during the manufacturing process.

Different frangible connections may be provided so long as the securement collar configuration that remains after the breaking does not compromise the proper function of the injection needle covering system. For example, rather than the triangular flanges 98 separated by openings 100, the frangible connection may be accomplished by differently shaped spanning elements, or by scoring an otherwise solid part.

Securement collar 80 is generally a cylindrical sleeve having an inner radial periphery 110 that defines an opening 112 which fits around boot mounting region 34. The outer radial periphery 114 of the lower or distal portion of collar 80 includes a hexagonal shape with flats 116 suitable for engagement by manufacturing tools. Chamfering 118 provided at the intersections of the flats 116 along their distal regions provides a more rounded contour for the distal facing surface of collar 80. The upper or proximal end 122 of collar 80 is sized to fit within annular hollow 70 of boot 22.

Although shown as having a continuous ring shape, the securement collar could be differently shaped. For example, and although such might be less robust, the ring shape could be interrupted by an axial or helical gap in its circumference while still providing its boot securing function.

With reference again to FIGS. 1-4, further details about the needled syringe 130 are provided. It will be appreciated that the shown configuration of the needled syringe 130 is intended to be illustrative and not limiting, as the inventive covering system may find beneficial application with differently configured needled syringes, including syringes having staked needles, syringes that include a cartridge, and syringes with different mechanisms for the syringe needle to be brought into fluid communication with the reservoir of the syringe.

Needled syringe 130 includes a barrel 140, a piston 144, a septum 155, a fitting 160, and a needle carrier 180. Barrel 140 is made of plastic and has an internal surface 142 that slidably accommodates an elastomeric piston 144 that seals the top of the syringe contents within the reservoir 146 of the barrel 140. A reduced diameter neck portion 150 of barrel 140 includes a distally projecting ring 152 at its distal end against which an elastomeric, sealing septum 155 is compressed by fitting 160. Sealing septum 155 is captured between ring 152 and an interior shoulder 162 of a hub portion 163 of fitting 160 when the fitting 160 is fixedly secured to barrel 140. Such fixed securement is achieved during manufacture by internally projecting dogs 164 of fitting 160 first being moved axially upward between L-shaped ribs 166 on the outer radial periphery of neck portion 150, and the fitting and barrel then being rotated relative to each other so that the dogs 164 align with shallow pockets in the upward facing surfaces of ribs 166. The axial force of the compressed septum 155 will act to retain dogs 164 in the pockets of ribs 166, forming a reinforced bayonette fitting.

Fitting 160 is formed as a single plastic piece of acetal and includes a stepped down, tubular protrusion 170 that extends from hub portion 163. The interior of protrusion 170 is hollow, which is adapted to hold needle carrier 180, and includes diametrically opposed channels 172 and diametrically opposed detents 174.

Fitting protrusion 170 includes a proximal region 200 and a distal region 202 that are connected by a tapering segment 204. Proximal region 200 has a cylindrical outer surface or periphery 201. A slight tapering in the radial direction as surface 201 extends distally aids in the boot being slid thereon during manufacture. Surface 201 serves as rigid support surface against which boot mounting region 34 can be pressed by securement collar 80.

A bar-shaped, plastic body 182 of carrier 180 slides within channels 172 and holds a rigid metal needle or cannula 184. The proximal tip 186 of needle 184 projects proximally from body 182 and is sharpened to pierce and pass through septum 155 during use so as to insert into the central opening 151 of barrel neck portion 150 to be in fluid communication with barrel reservoir 146. The distal tip 188 of needle 184 projects distally from body 182 and is sharpened to pierce and pass through boot distal end 26 and into a user to administer an injection. Resilient fingers 190 project from opposite sides of body 182 and each include indent regions 192 and 194 shaped to snap over fitting detents 174. Before use and as best shown in FIG. 2, needle carrier 180 is held within fitting 160 by indent regions 192 fitting over detents 174, in which configuration needle tip 186 is spaced from septum 155. When needle tip 188 penetrates an injection site and axial forces experienced by the needle carrier 180 cause the fingers 190 to cam inward such that the needle carrier can move axially farther into the fitting protrusion 170 until indent regions 194 snap fit over detents 174, the needle tip 186 has then moved through septum 155 and into opening 151 to allow fluid transport through needle 184 from reservoir 146.

The interior dimension of boot mounting region 34 normally will be selected by the manufacturer so that boot mounting region 34, on its own, has a frictional, sealing fit with support surface 201 of fitting 160. The interior dimension of securement collar 80 is selected by the manufacturer so that boot mounting region 34 is compressed against support surface 201 to further ensure a tight seal and make boot 22 more resistant to coming off syringe 130.

The needle covering system 20 can be attached to the needled syringe 130 during manufacture to provide protection for the needle and to facilitate further syringe handling. In particular, attachment typically occurs by the protective cover 85 first being maneuvered such that a boot 22, distinct from the rest of the needled syringe 130, has its body 30 fitted into the interior hollow of cover base 87 and such that collar end 122 inserts within hollow 70 to engage lip 65. The cover 85 with engaged boot 22 is then manipulated to mount it to a fitting 160, already equipped with a needle carrier 180, of needled syringe 130. Such fitting 160 with carrier 180 already may be attached to syringe barrel 140 as shown in FIG. 1, or alternatively may be separate from the syringe barrel 140, in which latter case the cover and engaged boot can be mounted together as a subassembly with the fitting with needle carrier, which fitting can then be gripped and mounted to the syringe barrel while capturing the septum 155 therebetween.

Mounting cover 85 with boot 22 to a fitting 160 holding carrier 180 involves maneuvering the cover and boot assembly axially so that the needle tip 188 inserts into boot pocket 60 sufficiently far to have boot mounting region 34 reach a sealing engagement with the fitting support surface 201. During this axial motion, collar 80 has the effect of pressing or sandwiching mounting region 34 tightly against fitting surface 201 to ensure a good and durable seal therewith. This axial motion does not cause needle carrier 180 to be moved farther into fitting 160.

Figure 7:
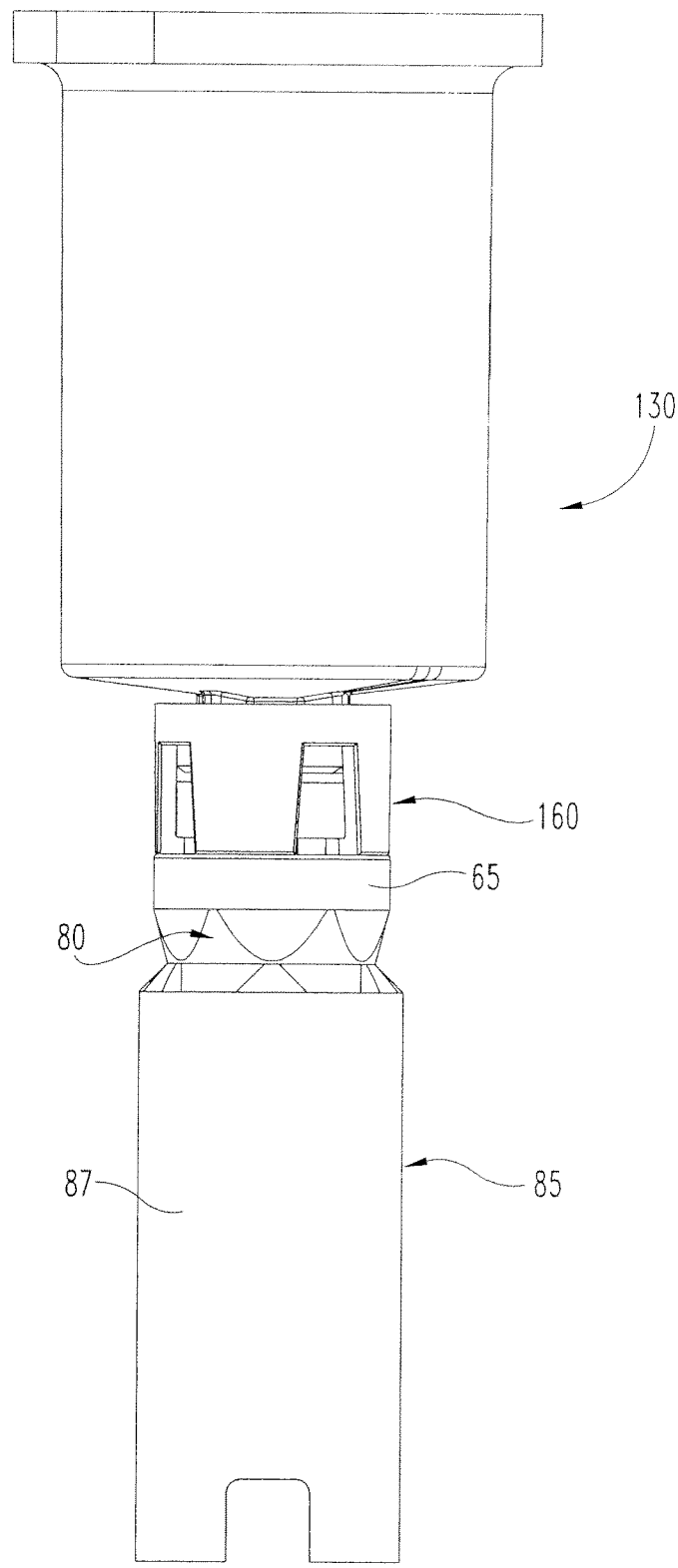
FIG. 7 is a front view of the needled syringe and injection needle covering system of FIG. 1 prior to the protective cover being broken and partially removed to leave only its remnant collar.

After this manufacturing process, the syringe barrel 130, septum 155, fitting 160 and cover 85 with engaged boot 22 can then be handled readily as a single unit and with the needle 184 protectively housed within boot 22 that is protectively housed within cover 85. The cover 85, due to its rigid relationship with the needled syringe, can support the syringe and be used as the piece held by the filling machine as the barrel 140 is filled with medicine and the piston 144 then inserted into barrel 140. At this point, the injection needle covering system 20 and needled syringe 130 are arranged as shown in FIGS. 7 and 8.

When the needled syringe 140 is to a point in manufacture at which the protective or handling features of cover 85 are no longer required, cover 85 is subjected to a controlled breaking operation. In this manner, base 87 and neck region 96 of cover 85 are broken off together, as a remainder portion, from securement collar 80 leaving collar 80 as a remnant in place securing boot mounting region 34 to fitting 160. Such controlled breakage can be achieved with a first tool gripping collar 80 via flats 116 and holding it to prevent rotation, and a second tool engaging cover body 87, such as via notches 90 or substituted openings, and providing a torque thereto to break it from collar 80. This controlled breakage does not disturb the seal protecting the needle as the breaking load is applied only to the collar 80 and the remainder portion of the cover 85. After such breakage, the remainder portion of the cover 85 may be removed and discarded, leaving the needled syringe and injection needle covering system as shown in FIG. 1 ready for use.

Figure 9:
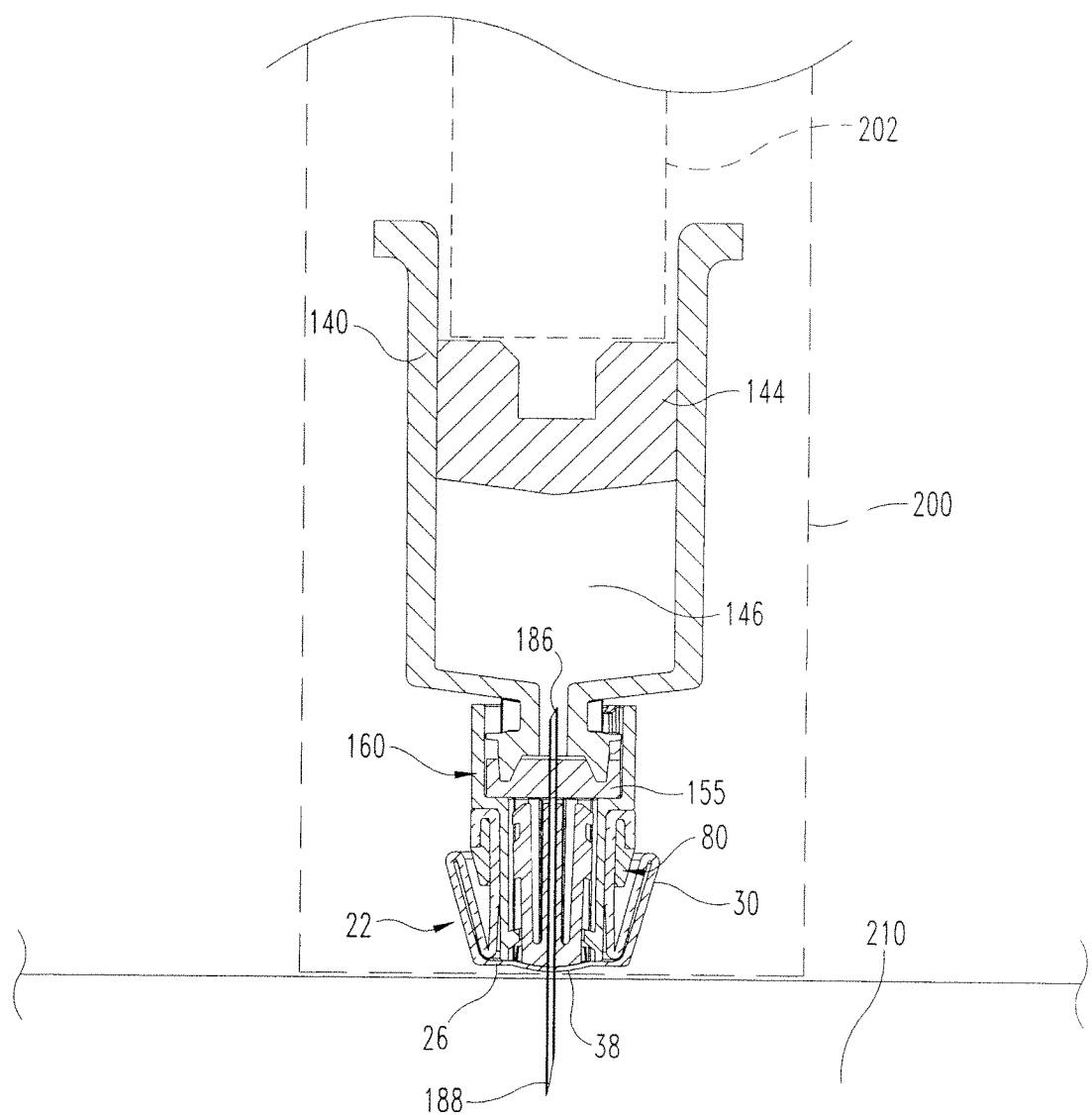
FIG. 9 is a longitudinal cross-sectional view of the needled syringe and injection needle covering system of FIG. 1 mounted in an injection device shown in dashed lines and in the process of injecting into an abstractly represented user.

A representative such use is to mount the assembly shown in FIG. 1 into an automatic injection device, for example a device in which the entire assembly shown in FIG. 1 is protectively held within a housing of the device before use and then driven downward within the device during use. When such device is operated, the needled syringe 130 is automatically driven downward such that the injection needle tip 188 pierces boot region 38 and projects beyond the bottom end of the device housing to penetrate a user. The boot body 30 collapses as the boot distal end 26 presses against an apertured end plate of the device. The proximal needle tip 186 communicates with the barrel reservoir 146, and the syringe plunger 144 is advanced by a drive piston of the device to inject the syringe contents into the user. This operation is represented in FIG. 9 where an abstractly shown automatic injection device having an outer housing represented by dash lines 200, and a drive piston represented in dash lines at 202, is shown forcing medication from the needle syringe reservoir 146 into a user indicated at 210.

Figure 10:
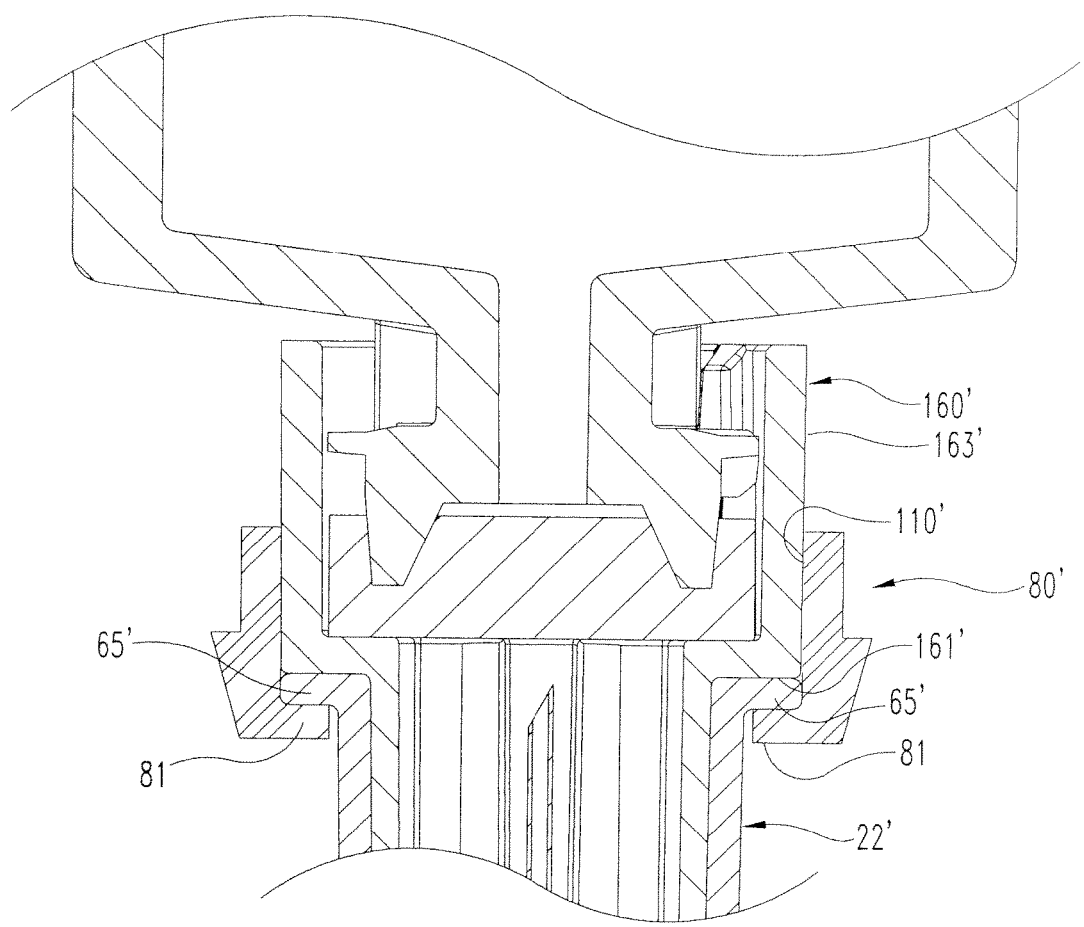
FIG. 10 is partial longitudinal cross-sectional view showing a needled syringe with an alternate injection needle covering system of the present invention.

Referring now to FIG. 10, another alternate embodiment of a needle covering system is shown in pertinent part after the remainder portion of the protective shell is removed. In this embodiment in which parts corresponding to the above embodiment are indicated with a prime reference, an axial seal as opposed to a radial seal is provided between the boot and the needled syringe. Securement collar 80' provides a rigid backing for the boot sealing ring portion by having its annular lip 81 press a horizontally only extending lip 65' of boot 22' against the underside 161' of hub portion 163' of fitting 160', which underside acts as the syringe support surface. Lip 65' thereby forms a continuous or three hundred sixty degree axial seal with underside 161'. Collar 80' is not mounted to the syringe via a friction fit afforded by the sandwiching or compression of the boot therebetween as with the embodiment of FIGS. 1-9, but rather is mounted directly to the syringe via a friction fit of collar inner radial periphery 110' with the exterior surface of fitting hub portion 163'. Interfitting connectors, such as snaps or threads or a bayonette type engagement, may be substituted for this frictional mounting.

While this invention has been shown and described as having preferred designs, the present invention may be modified within the spirit and scope of this disclosure. For example, while the securement collar and the rest of the protective shell are described above as being formed in one piece but disconneactable by the breaking of a frangible connection, such components and connection may be otherwise provided, as the collar and rest of the protective shell may be separately formed parts connected by mechanical connectors, such as snaps, which are disconnected to leave the collar securing the boot. In addition, the needle syringe 130 equipped with boot 22 and collar 80 is described above in use with one type of automatic injection device, but could be used, for example, with differently operating automatic injection devices. In addition, the boot could be adapted to seal the distal tip of the needle if used with a syringe in which the needle is in fluid communication with the syringe contents before use. This application is therefore intended to cover any variations, uses or adaptations of the invention using its general principles. Further, this application is intended to cover such departures from the present disclosure as come within known or customary practice in the art to which this invention pertains.

We claim:

1. A needle covering system for a needle of a syringe, the needle covering system comprising:
a boot defining a contaminant-proof pocket for the needle, said boot including a sealing ring portion, a needle pierceable end portion at a base of said pocket, and a body extending between said sealing ring portion and said needle pierceable end portion and having an interior hollow for the needle, said sealing ring portion disposed in a continuous circumferential sealing engagement with a support portion of the syringe, said body collapsible to allow movement of said needle pierceable end portion toward said sealing ring portion for a tip of the needle to pass through said needle pierceable end portion; and a securement collar configured to press said sealing ring portion against the support portion of the syringe, said securement collar being a remnant portion of a protective shell, said remnant portion remaining after a disconnection of said remnant portion from a remainder portion of the protective shell during manufacture and the remainder portion is removed from a protective position around said boot body.

2. The needle covering system of claim 1 wherein the connection between said remnant portion and said remainder portion of the protective shell is frangible, said frangible connection between said remnant portion and said remainder portion being broken during manufacture for the remainder portion to be removed.

3. The needle covering system of claim 2 wherein said boot comprises a one-piece construction from a resilient material.

4. The needle covering system of claim 2 wherein said securement collar comprises a ring shape.

5. The needle covering system of claim 4 wherein said securement collar encircles an outer circumference of said sealing ring portion of said boot.

6. The needle covering system of claim 5 wherein said securement collar comprises an outer radial periphery including plurality of tool engageable flats.

7. The needle covering system of claim 2 wherein said boot comprises a lip encircling and projecting in an outer radial direction from said sealing ring portion, said lip forming with said sealing ring portion an annular hollow in which inserts said securement collar.

8. The needle covering system of claim 2 wherein said boot body comprises first and second regions extending in an axial direction, said first region having a wall thickness that is thinner than a wall thickness of said second region to promote axial collapsing of said first region when said boot body collapses to allow movement of said needle pierceable end portion toward said sealing ring portion.

9. The needle covering system of claim 8 wherein said boot first region is disposed between said sealing ring portion and said boot second region, and wherein said securement collar is axially located clear of said boot second region.

10. The needle covering system of claim 9 wherein said securement collar is axially located clear of said boot first region.

11. The needle covering system of claim 2 wherein the remainder portion of the protective shell includes an interior hollow that accommodates said boot.

12. The needle covering system of claim 2 wherein said securement collar is mountable to the support portion by the sandwiching of the sealing ring portion therebetween.

13. The needle covering system of claim 1, wherein a proximal end of the sealing ring portion of said boot includes an outwardly protruding radial lip, and the securement collar includes a proximal end configured to engage against the outwardly protruding radial lip.

14. A needle covering system for a needle of a syringe, the syringe including a barrel having a neck, a fitting and a support portion of the fitting that is coupled to the neck of the barrel, the needle covering system comprising:

an axially collapsible boot defining a contaminant-proof pocket for the needle, said boot including a sealing ring proximal portion, a needle pierceable end distal portion at a base of said pocket, and a boot body extending between said sealing ring proximal portion and said needle pierceable end distal portion and having an interior hollow for the needle, wherein a proximal end of the sealing ring portion includes an outwardly protruding radial lip, said sealing ring portion structured to form a continuous seal with the support portion of the syringe, said boot body axially collapsible to allow movement of said needle pierceable end portion toward said sealing ring portion for a tip of the needle to pass through said needle pierceable end portion; and a removable cover to temporarily cover said needle, the removable cover having a protective configuration and a remnant configuration, wherein, in the protective configuration, the removable cover comprises a collar mounted around the boot, the collar configured to press said sealing ring portion of the boot against the support portion of the syringe, and a tubular base extending longitudinally from said collar over the boot to a distance sized to house said tip of the needle, wherein the collar and the tubular base are interconnected by a frangible connection, and wherein, in the remnant configuration, the collar remains secured to said sealing ring portion after removal of the tubular base along the frangible connection such that said boot is exposed.

15. The needle covering system of claim 14, wherein the collar is disposed to press said sealing ring portion of the boot against the support portion of the syringe that is distal to the neck of said syringe.

16. The needle covering system of claim 14, wherein the collar is configured to engage axially against the outwardly protruding radial lip.

17. The needle covering system of claim 14, wherein the outwardly protruding radial lip together with said sealing ring portion forms an annular hollow, wherein the collar is disposed within the annular hollow and engaging axially against the outwardly protruding radial lip.

18. The needle covering system of claim 14, wherein the tubular base includes one or more tool receiving features formed therein.

19. The needle covering system of claim 14, wherein said boot body comprises first and second regions extending in an axial direction, said first region having a wall thickness that is thinner than a wall thickness of said second region to promote axial collapsing of said first region when said boot body collapses to allow movement of said needle pierceable end portion toward said sealing ring portion, wherein said boot first region is disposed between said sealing ring portion and said boot second region.

20. The needle covering system of claim 19, wherein the boot includes a material without holes configured to provide a liquid-tight internal volume when sealing with the support portion of the syringe.

* * * * *